United States Patent
Rao et al.

(10) Patent No.: US 9,700,535 B2
(45) Date of Patent: Jul. 11, 2017

(54) ORAL PHARMACEUTICAL COMPOSITION OF ISOTRETINOIN

(71) Applicant: Sun Pharmaceutical Industries Limited, Mumbai, Maharashtra (IN)

(72) Inventors: Rajesh Rao, Uttar Pradesh (IN); Anuj Kumar Fanda, Uttar Pradesh (IN); Satish Kumar Jain, Chhattisgarh (IN); Romi Barat Singh, Uttar Pradesh (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 67 days.

(21) Appl. No.: 14/958,398

(22) Filed: Dec. 3, 2015

(65) Prior Publication Data
US 2016/0081964 A1    Mar. 24, 2016

Related U.S. Application Data

(63) Continuation of application No. PCT/IB2015/054101, filed on May 29, 2015.

(51) Int. Cl.
| | |
|---|---|
| *A61K 31/202* | (2006.01) |
| *A61K 9/48* | (2006.01) |
| *A61K 9/00* | (2006.01) |
| *A61K 9/16* | (2006.01) |
| *A61K 31/07* | (2006.01) |
| *A61K 31/203* | (2006.01) |

(52) U.S. Cl.
CPC .......... *A61K 31/202* (2013.01); *A61K 9/0053* (2013.01); *A61K 9/16* (2013.01); *A61K 9/48* (2013.01); *A61K 9/4833* (2013.01); *A61K 9/4858* (2013.01); *A61K 31/07* (2013.01); *A61K 31/203* (2013.01)

(58) Field of Classification Search
None
See application file for complete search history.

(56) References Cited

U.S. PATENT DOCUMENTS

| | | | |
|---|---|---|---|
| 5,993,858 A | 11/1999 | Crison et al. | 424/490 |
| 7,435,427 B2 | 10/2008 | Vanderbist et al. | 424/439 |
| 8,367,102 B2 | 2/2013 | Vanderbist et al. | 424/451 |
| 8,569,320 B2 | 10/2013 | Melzer et al. | 514/274 |
| 2005/0129773 A1 | 6/2005 | Bhatia et al. | 424/489 |
| 2014/0107203 A1 | 4/2014 | Deboeck et al. | 514/559 |

FOREIGN PATENT DOCUMENTS

| | | | |
|---|---|---|---|
| WO | WO 00/25772 | 5/2000 | A61K 31/203 |
| WO | WO 2010/134047 | 11/2010 | A61P 17/10 |
| WO | WO 2012/053013 | 4/2012 | A61K 9/107 |

OTHER PUBLICATIONS

Cipher Pharmaceuticals Inc., Epuris Product Monograph. Mar. 14, 2013 Available from : http://www.cipherpharma.com/download/epuris_july2015.pdf [accessed on Aug. 29, 2015].

*Primary Examiner* — Robert A Wax
*Assistant Examiner* — Randeep Singh

(57) ABSTRACT

An oral pharmaceutical composition of isotretinoin with reduced food effect. A process for preparing the oral pharmaceutical composition of the present invention.

21 Claims, No Drawings

ORAL PHARMACEUTICAL COMPOSITION OF ISOTRETINOIN

FIELD OF THE INVENTION

The present invention provides an oral pharmaceutical composition of isotretinoin with a reduced food effect. The present invention further relates to a process for preparing the oral pharmaceutical composition of the present invention.

BACKGROUND OF THE INVENTION

Isotretinoin is a retinoid (also known as 13-cis retinoic acid). Owing to its low water solubility, the oral bioavailability of isotretinoin is low. PCT Publication No. WO 00/25772 discloses that the presently marketed formulation of isotretinoin, i.e., Accutane®, contains isotretinoin at a mean particle size of about 100 μm resulting in only 20% oral bioavailability. Therefore, this application discloses a formulation of isotretinoin having a reduced particle size, thereby enhancing the oral bioavailability.

U.S. Pat. Nos. 7,435,427 and 8,367,102 cover the marketed formulation of Absorica®. These patents disclose capsules comprising a semi-solid suspension of isotretinoin containing at least two lipidic excipients, one having an HLB value equal to or greater than 10 and the other being an oily vehicle. These patents are based on the use of the "Lidose technology" to provide a formulation of isotretinoin with enhanced bioavailability.

The oral bioavailability of a drug is affected by various factors, which include aqueous solubility, absorption of drug through gastrointestinal tract, first pass effect, or food effect. The "food effect" as used herein means food-drug interactions which either decrease or increase the extent of drug absorption. Isotretinoin is known to have a food effect, i.e., its absorption is dependent on the presence of the food in the stomach. Therefore, there is a need to develop a composition of isotretinoin which exhibits a reduced food effect.

SUMMARY OF THE INVENTION

The present invention provides an oral pharmaceutical composition comprising isotretinoin wherein said composition exhibits a reduced food effect. The present invention further provides an oral pharmaceutical composition comprising:
  a) isotretinoin;
  b) one or more surfactants having HLB value of 10 or greater; and
  c) one or more co-solvents
wherein said composition is substantially free of oil.

The present composition is in the form of a dispersion which is further filled into capsules. The present invention further provides a process for preparing the oral pharmaceutical composition of the present invention. It also provides a method of treating acne by administering the oral pharmaceutical composition of the present invention.

DETAILED DESCRIPTION OF THE INVENTION

In one aspect, the present invention provides an oral pharmaceutical composition comprising isotretinoin wherein said composition exhibits a reduced food effect.

In one embodiment of the above aspect, said composition exhibits reduced food effect in comparison to the marketed Epuris™ capsules as indicated by higher $C_{max}$ and AUC in fasting state.

In another embodiment of the above aspect, said composition exhibits a mean $C_{max}$ under fasting condition which is about 1.9 times higher than the $C_{max}$ of Epuris™ capsules.

In another embodiment of the above aspect, said composition exhibits a mean AUC under fasting condition which is about 1.7 times higher than the AUC of Epuris™ capsules.

In another embodiment of the above aspect, the composition, when administered orally, has a mean fed/fasted ratio of AUC of about 1.26 and a mean fed/fasted ratio of $C_{max}$ of about 1.10.

In another aspect, the present invention provides an oral pharmaceutical composition comprising:
  a) isotretinoin;
  b) one or more surfactants having HLB value of 10 or greater; and
  c) one or more co-solvents
wherein said composition is substantially free of oil.

In one embodiment of the above aspect, said composition comprises isotretinoin in an amount of about 1 mg to 100 mg, 5 mg to 50 mg, 10 mg to 40 mg, 9 mg to 36 mg, or 8 mg to 32 mg.

In another embodiment of the above aspect, said composition comprises isotretinoin in an amount of about 40 mg.

In another embodiment of the above aspect, said composition comprises isotretinoin in an amount of about 36 mg.

In another embodiment of the above aspect, said composition comprises isotretinoin in an amount of about 32 mg.

In another embodiment of the above aspect, said composition comprises isotretinoin in an amount of about 16 mg.

In one embodiment of the above aspect, said surfactants include, but are not limited to, polysorbates prepared from lauric, palmitic, stearic, and oleic acid; polyoxyethylene monoesters such as polyoxyethylethylene monostearate, polyoxyethylene monolaurate, and polyoxyethylene monooleate; polyethoxylated castor oils (e.g., Cremophor® EL 35); polyethylene glycol glycerides (e.g., Gelucire® 44/14); vitamin E TPGS; dioctyl sodium sulfosuccinate; sodium lauryl sulfate; poloxamers; and mixtures thereof.

In another embodiment of the above aspect, the surfactant is present in an amount of about 1% w/w to about 99% w/w by total weight of the composition; preferably in an amount of about 10% w/w to about 80% w/w by total weight of the composition; more preferably in an amount of about 30% w/w to about 80% w/w by total weight of the composition.

In another embodiment of the above aspect, said co-solvents include, but are not limited to, propylene glycol, polypropylene glycol, polyethylene glycols, diethyleneglycol monoethyl ether, glyceryl caprylate, capric/caprylic glyceride, and mixtures thereof.

In another embodiment of the above aspect, the composition further comprises an antioxidant.

The antioxidant includes, but is not limited to, butylated hydroxy anisole, butylated hydroxy toluene, tocopherol, ascorbyl palmitate, ascorbic acid, sodium metabisulfite, sodium sulfite, sodium thiosulfate, propyl gallate, and mixtures thereof.

In one embodiment of the above aspect, the oral pharmaceutical composition is in the form of a dispersion which is further filled into capsules.

In yet another embodiment of the above aspect, the composition comprises isotretinoin wherein the particle size distribution of isotretinoin is such that $D_{90}$ is less than 60 μm, less than 55 μm, less than 50 μm, less than 45 μm, less than 40 µm, less than 35 µm, less than 30 µm, less than 25 µm, less than 20 µm, less than 15 µm, or less than 10 µm.

In yet another embodiment of the above aspect, the composition comprises isotretinoin wherein the particle size distribution of isotretinoin is such that $D_{90}$ is less than 30 µm.

In another embodiment of the above aspect, the composition comprises isotretinoin wherein the particle size distribution of isotretinoin is such that $D_{50}$ is less than 40 µm, less than 35 µm, less than 30 µm, less than 25 µm, less than 20 µm, less than 15 µm, or less than 10 µm or less than 5 µm.

In yet another embodiment of the above aspect, the composition comprises isotretinoin wherein the particle size distribution of isotretinoin is such that $D_{50}$ is less than 15 µm.

In another embodiment of the above aspect, the composition comprises isotretinoin wherein the particle size distribution of isotretinoin is such that $D_{10}$ is less than 20 µm, less than 18 µm, less than 17 µm, less than 15 µm, less than 12 µm, less than 10 µm, less than 8 µm, less than 7 µm, less than 5 µm, or less than 2 µm.

In yet another embodiment of the above aspect, the composition comprises isotretinoin wherein the particle size distribution of isotretinoin is such that $D_{10}$ is less than 7 µm.

In yet another embodiment of the above aspect, the oral pharmaceutical composition comprises isotretinoin wherein the particle size distribution of isotretinoin is such that $D_{90}$ is less than 60 µm and $D_{50}$ is less than 40 µm.

In yet another embodiment of the above aspect, the oral pharmaceutical composition comprises isotretinoin wherein the particle size distribution of isotretinoin is such that $D_{90}$ is less than 60 µm, $D_{50}$ is less than 40 µm, and $D_{10}$ is less than 20 µm.

In yet another embodiment, said oral pharmaceutical composition is stable when stored at 40° C. and 75% relative humidity or at 25° C. and 60% relative humidity for a period of at least three months or to the extent necessary for the use of the composition.

In yet another aspect, there is provided a process for the preparation of an oral pharmaceutical composition wherein the process comprises:
(a) adding one or more of surfactants in a co-solvent or a mixture of co-solvents;
(b) dispersing isotretinoin into the solution of step (a);
(c) milling the dispersion of step (b) in a milling apparatus; and
(d) filling the milled dispersion of step (d) into a capsule.

In an embodiment of the above aspect, an antioxidant is added in step (a) of the process.

In still another aspect, the present invention provides a method of treating acne, musculoskeletal and connective tissue inflammations, emphysema, ulcerating diseases, cervical tumors in HIV positive women, lung cancer in smokers, skin cancer, neuroblastoma, recurrent prostate cancer, leukemia, high-grade glioma, head and neck cancers, multiple myeloma, gram-negative folliculitis, recalcitrant rosacea, pyoderma faciale, psoriasis, cutaneous lupus erythematosus, acne fulminans, squamous cell carcinoma, or cutaneous photoaging by administering to the individual in need thereof the oral pharmaceutical composition of the present invention.

In one embodiment of the above aspect, the present invention provides a method of treating acne by administering to the individual in need thereof the oral pharmaceutical composition of the present invention.

The term "isotretinoin" refers to isotretinoin in its crystalline or amorphous form, its esters, salts, or derivatives thereof.

The term "stable," as used herein, refers to chemical stability, wherein not more than 1.5% w/w of total related substances are formed on storage at accelerated conditions of stability at 40° C. and 75% relative humidity or at 25° C. and 60% relative humidity for a period of at least three months or to the extent necessary for use of the composition.

The term "AUC" refers to the area under the time/plasma concentration curve after administration of the pharmaceutical composition. $AUC_{0\text{-}infinity}$ denotes the area under the plasma concentration versus time curve from time 0 to infinity; $AUC_{0\text{-}t}$ denotes the area under the plasma concentration versus time curve from time 0 to time t.

The term "$C_{max}$" refers to the maximum concentration of isotretinoin in the blood following administration of the pharmaceutical composition.

The term "$t_{max}$" refers to the time in hours when $C_{max}$ is achieved following administration of the pharmaceutical composition.

The term "food effect" as used herein means food-drug interactions which either decrease or increase the extent of drug absorption. It refers to a relative difference in AUC, $C_{max}$, and/or $t_{max}$ of a drug, when said drug or a formulation thereof is administered orally to a human concomitantly with food or in a fed state as compared to the same values when the same formulation is administered in a fasted state or without food.

The term "$D_{10}$" refers to the particle size of isotretinoin where 10% (w/v) of the particles have a size less than the defined $D_{10}$ value; "$D_{50}$" refers to the particle size of isotretinoin where 50% (w/v) of the particles have a size less than the defined $D_{50}$ value; "$D_{90}$" refers to the particle size of isotretinoin where 90% (w/v) of the particles have a size less than the defined $D_{90}$ value.

"Defined $D_{10}$ value/$D_{50}$ value/$D_{90}$ value" refers to the values defined in the embodiments.

The term "substantially free of oil" includes the complete absence of oil and the presence of less than 5% of oil.

The size reduction of isotretinoin is achieved by wet milling the dispersion of isotretinoin in an oily vehicle or the dispersion of isotretinoin in an aqueous medium using mechanical means such as a ball mill, and media mills such as a sand mill, DYNO®-mill, or a bead mill. The grinding media in these mills can comprise spherical particles such as stainless steel beads or zirconium oxide balls.

The invention may be further illustrated by the following examples, which are for illustrative purposes only and should not be construed as limiting the scope of the invention in any way.

EXAMPLES

Example 1

| Ingredients | Quantity (% w/w) |
| --- | --- |
| Isotretinoin | 6.61 |
| Cremophor ® EL 35 | 57.02 |
| Tween ® 80 | 3.30 |
| Butylated hydroxy toluene | 0.09 |
| Propyl gallate | 0.05 |
| Propylene glycol | 23.96 |
| Vitamin E TPGS | 8.92 |

Procedure:
1. Cremophor® EL 35, Tween® 80, and propylene glycol were mixed in a stainless steel vessel.
2. Butylated hydroxy toluene and propyl gallate were added to the mixture of step 1.
3. Isotretinoin was dispersed under stirring into the mixture of step 2.
4. The dispersion of step 3 was milled in a Dyno®-Mill containing zirconium beads to achieve a particle size of isotretinoin such that $D_{90}$ was about 22 μm.
5. Vitamin E TPGS was melted at a temperature not exceeding 80° C.
6. The milled dispersion of step 4 was heated to below 50° C. under continuous stirring.
7. The melted vitamin E TPGS of step 5 was added under stirring to the heated milled dispersion of step 6.
8. The dispersion of step 7 was filled into capsules.

Example 2

| Ingredients | Quantity (% w/w) |
|---|---|
| Isotretinoin | 5.40 |
| Cremophor ® EL 35 | 46.62 |
| Tween ® 80 | 2.70 |
| Butylated hydroxy toluene | 0.07 |
| Propyl gallate | 0.04 |
| Propylene glycol | 19.59 |
| Vitamin E TPGS | 7.29 |
| Gelucire ® 44/14 | 18.24 |

Procedure:
1. Cremophor® EL 35, Tween® 80, and propylene glycol were mixed in a stainless steel vessel.
2. Butylated hydroxy toluene and propyl gallate were added to the mixture of step 1.
3. Isotretinoin was dispersed under stirring into the mixture of step 2.
4. The dispersion of step 3 was milled in a Dyno®-Mill containing zirconium beads to achieve a particle size of isotretinoin such that $D_{90}$ was about 22 μm.
5. Vitamin E TPGS was melted at a temperature not exceeding 80° C.
6. The milled dispersion of step 4 was heated to below 50° C. with continuous stirring.
7. The melted vitamin E TPGS of step 5 was added under stirring to the heated milled dispersion of step 6.
8. Gelucire® 44/14 was melted at a temperature not exceeding 80° C. and added under stirring to the dispersion of step 7.
9. The dispersion of step 8 was filled into capsules.

Dissolution Studies

The pharmaceutical composition of Example 2 (Test; 40 mg of isotretinoin) was compared with the marketed formulation of isotretinoin (Reference; 40 mg Epuris™ capsules) for the release profile in the FDA recommended dissolution medium as given below:

| Dissolution Media | 0.05M buffer pH 7.8 with 0.5% w/v N,N-dimethyl dodecylamine N-oxide |
|---|---|
| Apparatus/RPM/Vol | USP Type I (20 mesh basket)/100/900 mL |

| | % of Drug Released in time (minutes) | | | | | | |
|---|---|---|---|---|---|---|---|
| Sample | 15 | 30 | 45 | 60 | 90 | 120 | 180 |
| Test | 84 | 94 | 94 | 94 | 95 | 97 | 98 |
| Reference | 1 | 9 | 24 | 49 | 89 | 100 | 100 |

From the above data, it is evident that the test product has a better dissolution profile in comparison to the reference product.

Pharmacokinetic Study Under Fed Condition

The pharmaceutical composition of Example 2 (Test; 40 mg of isotretinoin) was compared with the marketed formulation of isotretinoin (Reference; 40 mg Epuris™ capsules) under fed conditions on 18 healthy adult male subjects, out of these, 15 subjects completed all the three periods of the study.

Values for various pharmacokinetic parameters, including observed $C_{max}$, $AUC_{0-t}$ and $AUC_{0-inf}$ were calculated and are provided in Table 1 below.

TABLE 1

Comparative pharmacokinetic data for test (T) and reference (R) in 15 healthy adult human male subjects:

| | In $C_{max}$ | In $AUC_{0-t}$ | In $AUC_{0-inf}$ |
|---|---|---|---|
| Ratio (T/R) | 111.56 | 106.31 | 106.67 |
| 90% CI | 100.31-124.07 | 101.7-111.12 | 102.3-111.22 |

Average $t_{max}$ values for the Test and Reference were 3.6443 hours and 6.1444 hours, respectively.

Under fed conditions, the Test prototype showed a comparable behavior to the Reference product (Epuris™) in terms of both rate and extent of absorption. The T/R ratios and 90% CIs for all PK parameters are within the acceptable limits of 80% to 125%.

Pharmacokinetic Study Under Fasting Condition

The pharmaceutical composition of Example 2 (Test; 40 mg of isotretinoin) was compared with the marketed formulation of isotretinoin (Reference; 40 mg Epuris™ capsules) under fasting conditions in 18 healthy adult male subjects, out of these 14 subjects completed all the three periods of the study.

Values for various pharmacokinetic parameters, including observed $C_{max}$, $AUC_{0-t}$ and $AUC_{0-inf}$ were calculated and are provided in Table 2 below:

TABLE 2

Comparative pharmacokinetic data for Test (T) vs Reference (R) in 14 healthy adult human male subjects:

| | In $C_{max}$ | In $AUC_{0-t}$ | In $AUC_{0-inf}$ |
|---|---|---|---|
| Ratio (T/R) | 193.23 | 179.26 | 175.24 |
| 90% CI | 157.56-236.98 | 156.77-204.98 | 154.3-199.01 |

Test has shown 1.9-fold higher $C_{max}$ and 1.7-fold higher AUC as compared to Reference under fasting condition.

The Effect of Food on the Test Formulation of Example 2 (40 mg Capsules) was Also Evaluated and Results are Provided in Table 3 Below:

Reference (R): Epuris™ 40 mg capsules.
Test (T): Isotretinoin 40 mg capsules (Example 2).

TABLE 3

Relative effect of food (Calculated in number of fold (fed/fasting))

| Formulation | $C_{max}$ | $AUC_{0-t}$ |
|---|---|---|
| Test (T fed/fast) | 1.10 | 1.26 |
| Reference (R fed/fast) | 1.95 | 2.12 |

Above data indicates the following:

For Test prototype the AUC under fed condition is approximately 1.26-fold the value observed under fasting condition, whereas $C_{max}$ under fed condition is approx. 1.1-fold higher as compared to fasting condition.

For Epuris™, both AUC and $C_{max}$ under fed condition are ~2-fold higher than under fasted condition.

Example 3

| Ingredients | Quantity (% w/w) |
|---|---|
| Isotretinoin | 5.00 |
| Cremophor ® EL 35 | 37.50 |
| Tween ® 80 | 4.37 |
| Butylated hydroxy anisole | 0.12 |
| Propylene glycol | 18.12 |
| Vitamin E TPGS | 12.50 |
| Gelucire ® 44/14 | 22.43 |

Procedure:
1. Cremophor® EL 35, Tween® 80, and propylene glycol were mixed in a stainless steel vessel.
2. Butylated hydroxy anisole was added to the mixture of step 1.
3. Isotretinoin was dispersed under stirring into the mixture of step 2.
4. The dispersion of step 3 was milled in a Dyno®-Mill containing zirconium beads to achieve a particle size of isotretinoin such that $D_{90}$ was about 22 μm.
5. Vitamin E TPGS was melted at a temperature not exceeding 80° C.
6. The milled dispersion of step 4 was heated to below 50° C. with continuous stirring.
7. The melted vitamin E TPGS of step 5 was added under stirring to the heated milled dispersion of step 6.
8. Gelucire® 44/14 was melted at a temperature not exceeding 80° C. and added under stirring to the dispersion of step 7.
9. The dispersion of step 8 was filled into capsules.

Example 4

| Ingredients | Quantity (% w/w) |
|---|---|
| Isotretinoin | 5.40 |
| Cremophor ® EL 35 | 46.62 |
| Tween ® 80 | 2.70 |
| Butylated hydroxy toluene | 0.07 |
| Propyl gallate | 0.04 |
| Propylene glycol | 9.795 |
| Polyethylene glycol | 9.795 |
| Vitamin E TPGS | 7.29 |
| Gelucire ® 44/14 | 18.24 |

Procedure:
1. Cremophor® EL 35, Tween® 80, polyethylene glycol, and propylene glycol were mixed in a stainless steel vessel.
2. Butylated hydroxy toluene and propyl gallate were added to the mixture of step 1.
3. Isotretinoin was dispersed under stirring into the mixture of step 2.
4. The dispersion of step 3 was milled in a Dyno®-Mill containing zirconium beads to achieve a particle size of isotretinoin such that $D_{90}$ was about 22 μm.
5. Vitamin E TPGS was melted at a temperature not exceeding 80° C.
6. The milled dispersion of step 4 was heated to below 50° C. with continuous stirring.
7. The melted vitamin E TPGS of step 5 was added under stirring to the heated milled dispersion of step 6.
8. Gelucire® 44/14 was melted at a temperature not exceeding 80° C. and added under stirring to the dispersion of step 7.
9. The dispersion of step 8 was filled into capsules.

Example 5

| Ingredients | Quantity (% w/w) |
|---|---|
| Isotretinoin | 5.41 |
| Cremophor ® EL 35 | 46.63 |
| Tween ® 80 | 2.70 |
| Butylated hydroxy toluene | 0.08 |
| Propyl gallate | 0.05 |
| Propylene glycol | 9.80 |
| Polyethylene glycol | 9.80 |
| Vitamin E TPGS | 7.30 |
| Gelucire ® 44/14 | 18.24 |

Procedure
1. Cremophor® EL 35, Tween® 80, polyethylene glycol, Gelucire® 44/14, vitamin E TPGS, and propylene glycol were mixed in a stainless steel vessel with gentle heating below 50° C.
2. Butylated hydroxy toluene and propyl gallate was added to the mixture of step 1.
3. Isotretinoin was dispersed under stirring into the mixture of step 2.
4. The dispersion of step 3 was milled in a Dyno®-Mill containing zirconium beads to achieve a particle size of isotretinoin such that $D_{90}$ was about 10 μm.
5. The dispersion of step 4 was filled into capsules.

We claim:
1. An oral pharmaceutical composition comprising micronized isotretinoin having $d_{90}$ value of not more than 30 microns, wherein said composition is in the form of dispersion in a liquid vehicle and exhibits reduced food effect when administered orally and has a mean fed/fasted ratio of AUC of about 1.26 and a mean fed/fasted ratio of $C_{max}$ of about 1.10.

2. The oral pharmaceutical composition according to claim 1, wherein said composition comprises:
   a) isotretinoin;
   b) one or more surfactants having HLB value of 10 or greater; and
   c) one or more co-solvents
   wherein said composition is substantially free of oil.

3. The oral pharmaceutical composition according to claim 2, wherein said composition comprises isotretinoin in an amount of about 1 mg to 100 mg, 5 mg to 50 mg, 10 mg to 40 mg, 9 mg to 36 mg, or 8 mg to 32 mg.

4. The oral pharmaceutical composition according to claim 3, wherein said composition comprises isotretinoin in an amount of about 40 mg, about 36 mg, about 32 mg, about 28 mg, about 24 mg, about 20 mg, about 16 mg, or about 8 mg.

5. The oral pharmaceutical composition according to claim 2, wherein the surfactant is selected from the group consisting of polysorbates prepared from lauric, palmitic, stearic, and oleic acid; polyoxyethylene monoesters; polyethoxylated castor oils; polyethylene glycol glycerides; Vitamin E TPGS; dioctyl sodium sulfosuccinate; sodium lauryl sulfate; poloxamers; and mixtures thereof.

6. The oral pharmaceutical composition according to claim 5, wherein the surfactant is present in an amount of about 1% w/w to about 99% w/w by total weight of the composition.

7. The oral pharmaceutical composition according to claim 6, wherein the surfactant is present in an amount of about 30% w/w to about 80% w/w by total weight of the composition.

8. The oral pharmaceutical composition according to claim 2, wherein the co-solvent is selected from the group consisting of propylene glycol, polypropylene glycol, polyethylene glycols, diethyleneglycol monoethyl ether, glyceryl caprylate, capric/caprylic glyceride, and mixtures thereof.

9. The oral pharmaceutical composition according to claim 2, wherein said composition further comprises an antioxidant.

10. The oral pharmaceutical composition according to claim 9, wherein the antioxidant is selected from the group consisting of butylated hydroxy anisole, butylated hydroxy toluene, tocopherol, ascorbyl palmitate, ascorbic acid, sodium metabisulfite, sodium sulfite, sodium thiosulfate, propyl gallate, and mixtures thereof.

11. The oral pharmaceutical composition according to claim 2, wherein said composition is in the form of a dispersion which is further filled into capsules.

12. The oral pharmaceutical composition according to claim 1, wherein the particle size distribution of isotretinoin is such that $D_{90}$ is less than 30 μn, less than 25 μm, less than 20 μm, less than 15 μm, or less than 10 μm.

13. The oral pharmaceutical composition according to claim 1, wherein the particle size distribution of isotretinoin is such that $D_{50}$, less than 20 μm, less than 15 μm, less than 10 μm, or less than 5 μm.

14. The oral pharmaceutical composition according to claim 13, wherein the particle size distribution of isotretinoin is such that $D_{50}$ is less than 15 μm.

15. The oral pharmaceutical composition according to claim 1, wherein the particle size distribution of isotretinoin is such that $D_{10}$ is less than 10 μm, less than 8 μm, less than 7 μm, less than 5 μm, or less than 2 μm.

16. The oral pharmaceutical composition according to claim 15, wherein the particle size distribution of isotretinoin is such that $D_{10}$ is less than 7 μm.

17. The oral pharmaceutical composition according to claim 1, wherein said composition is stable when stored at 40° C. and 75% relative humidity or at 25° C. and 60% relative humidity for a period of at least three months.

18. The oral pharmaceutical composition according to claim 1, wherein said composition is used for the treatment of acne, musculoskeletal and connective tissue inflammations, emphysema, ulcerating diseases, cervical tumors in HIV positive women, lung cancer in smokers, skin cancer, neuroblastoma, recurrent prostate cancer, leukemia, high-grade glioma, head and neck cancers, multiple myeloma, gram-negative folliculitis, recalcitrant rosacea, pyoderma faciale, psoriasis, cutaneous lupus erythematosus, acne fulminans, squamous cell carcinoma, or cutaneous photoaging.

19. The oral pharmaceutical composition according to claim 18, wherein said composition is used for the treatment of acne.

20. The oral pharmaceutical composition according to claim 1, wherein said composition releases more than 50% of isotretinoin in 15 minutes in a media with a pH of 7.8.

21. A capsule composition of micronized isotretinoin having a $d_{90}$ value not more than 30 microns, wherein said composition is in the form of dispersion in a liquid vehicle and exhibits reduced food effect when administered orally and has a mean fed/fasted ratio of $C_{max}$ of about 1.10.

* * * * *